(12) United States Patent
Fobi et al.

(10) Patent No.: US 8,469,978 B2
(45) Date of Patent: *Jun. 25, 2013

(54) GASTRIC BYPASS BAND AND SURGICAL METHOD

(75) Inventors: Mathias Asongwe Lawrence Fobi, Rolling Hills, CA (US); C. Bruce Fields, Roseville, CA (US); Jean E. Fields, legal representative, Roseville, CA (US)

(73) Assignee: Bariatec Corporation, Palos Verdes Pennisula, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,018

(22) Filed: Mar. 21, 2011

(65) Prior Publication Data

US 2011/0208216 A1    Aug. 25, 2011

Related U.S. Application Data

(63) Continuation of application No. 10/876,397, filed on Jun. 24, 2004, now Pat. No. 7,909,839.

(60) Provisional application No. 60/574,741, filed on May 26, 2004.

(51) Int. Cl.
*A61B 17/08* (2006.01)

(52) U.S. Cl.
USPC ............................ 606/157; 606/151

(58) Field of Classification Search
USPC ......... 606/151, 157, 158; 600/30, 37; 24/662, 24/17 AP, 16 PB, 30.5 P, 910, 115 R, 129 R, 24/130, 132 R, 136 R, 115 N; 63/11, 15.3, 63/3.1
See application file for complete search history.

(56) References Cited

U.S. PATENT DOCUMENTS 3,875,928 A   4/1975   Angelchik .................. 600/37
4,592,339 A   6/1986   Kuzmak et al. ............. 128/899

(Continued)

FOREIGN PATENT DOCUMENTS

EP      1 036 545 A2       9/2000
WO      WO 94/27504       12/1994
WO      WO 03/057092 A2    7/2003

OTHER PUBLICATIONS

EP, Search Report for PCT/US2005008710, Nov. 6, 2009.

(Continued)

*Primary Examiner* — Corrine M McDermott
*Assistant Examiner* — Melissa Ryckman
(74) *Attorney, Agent, or Firm* — Dickstein Shapiro LLP; Kenneth S. Roberts

(57) ABSTRACT

An inventive method for performing gastric bypass surgery and a gastric bypass band that is used in conjunction with the surgical method is disclosed. The inventive method involves separating a top portion of the stomach along with the esophagus from the remainder of the stomach, and re-connecting the separated portion to the small intestine to form a gastric pouch of about 20-30 cc in size. The inventive gastric band is placed midway along the gastric pouch to act as a restrictor valve to limit the amount of food passing through the valve. The band also retains food within the gastric pouch to give the patient a feeling of satiety. The band is comprised of an expansion-resistant section combined with a one-way latch mechanism. The latch has a curved orientation so that the band is formed into a radial profile when placed around the gastric pouch.

9 Claims, 3 Drawing Sheets

U.S. PATENT DOCUMENTS

| | | | |
|---|---|---|---|
| 4,958,791 A | 9/1990 | Nakamura | 248/74.1 |
| 5,601,604 A | 2/1997 | Vincent | |
| 5,771,903 A | 6/1998 | Jakobsson | |
| 6,432,040 B1 | 8/2002 | Meah | |
| 6,572,627 B2 | 6/2003 | Gabbay | |
| 6,676,674 B1 | 1/2004 | Dudai | |
| 2005/0038458 A1* | 2/2005 | Bailly et al. | 606/157 |
| 2005/0075652 A1 | 4/2005 | Byrum et al. | 606/139 |
| 2005/0251181 A1 | 11/2005 | Bachmann | 606/157 |

OTHER PUBLICATIONS

Mathias A.L. Fobi, MD, FACS et al., "Band Erosion: Incidence, Etiology, Management and Outcome after Banded Vertical Gastric Bypass," Obesity Surgery, vol. 11, pp. 1-9 (2001) USA (see Fig. 10, Fig. 5; pp. 1, 5, and 7).

Mathias A.L. Fobi, MD, FACS "Placement of the GaBP Ring System in the Banded Gastric Bypass Operation," Obesity Surgery, vol. 15, 1196-1201 (2005) USA (see p. 1197).

Inamed Lap Band Advertisement and Website.

Heliogast Advertisement and Website.

BM Pro-Ring Advertisement and Website.

Midband Advertisement.

Siliband Website.

Swedish Adjustable Gastric Band Advertisement.

\* cited by examiner

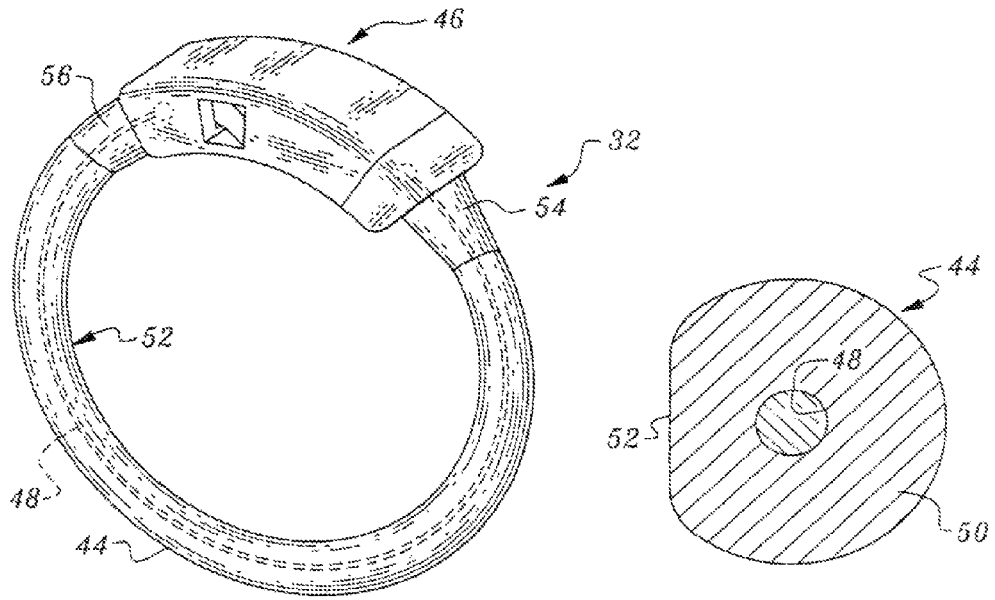
Fig. 3    Fig. 4
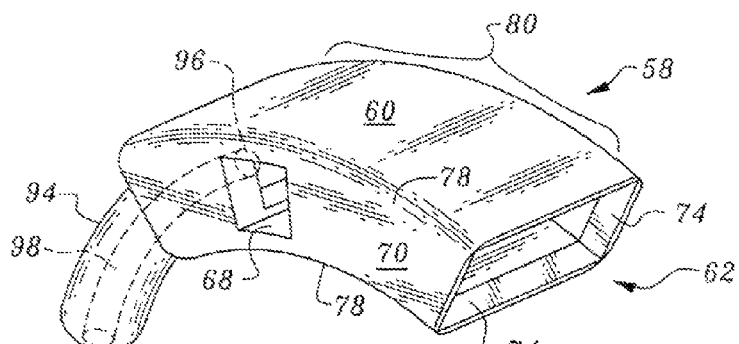
Fig. 5A
Fig. 5B

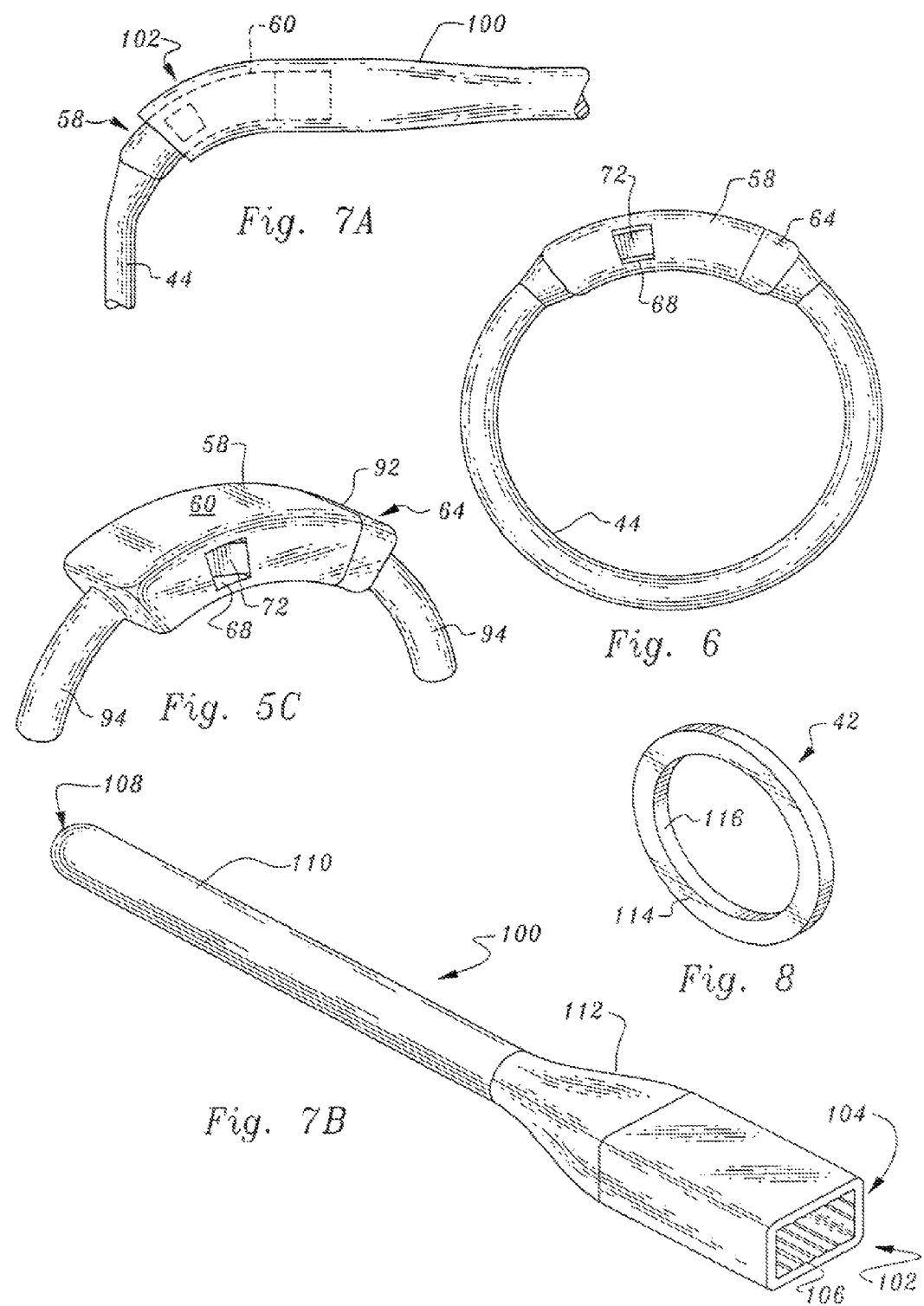

GASTRIC BYPASS BAND AND SURGICAL METHOD

CROSS REFERENCE TO RELATED APPLICATIONS

This application is a continuation of U.S. application Ser. No. 10/876,397 filed Jun. 24, 2004, now U.S. Pat. No. 7,909,839, which claims the benefit of U.S. Provisional Ser. No. 60/574,741 filed on May 26, 2004, which applications are fully incorporated herein by reference.

TECHNICAL FIELD

The present invention pertains to devices for performing gastric bypass surgery for morbidly obese individuals, and more specifically, to a gastric bypass band which creates a small gastric pouch from the esophagus and a portion of the proximal stomach. This invention also details the gastric bypass surgery method that is performed in conjunction with the application of the gastric bypass band.

BACKGROUND

In the United States, obesity affects the health of 80 million adults, or 35 percent of the adult population, according to statistics from the Centers for Disease Control and Prevention. American children are also becoming increasingly affected by obesity, as 9 million, or 15 percent of the child population has fallen victim to this disease in recent years.

Morbidly obese individuals are identified as those where the disease of obesity has advanced to where the individual has a Body Mass Index (BM1) of over 40 or a BMI of over 35 along with other "co-morbidities" such as diabetes or high blood pressure. To reach a BMI of 35, a 5-foot-10-inch man or a 5-foot-4-inch woman would need to weigh 243 pounds and 204 pounds, respectively. For these individuals, dieting has often become a futile effort, as while some pounds may be shed, over time it has been found that these pounds are often quickly regained. Due to the health threats posed by their condition, morbidly obese individuals have turned to gastric bypass surgery in increasing numbers as an effective method to lose weight.

There are a number of methods of gastric bypass surgery, as well as a number of medical appliances which have been developed to assist in the application of these methods. However, most methods of gastric bypass surgery operate on the theme of creating a reduced-size "gastric pouch" out of the stomach, which remains connected to the small intestine. The pouch restricts the amount of food entering the body to a fraction of what would normally enter an unrestricted stomach. Once the pouch is full, the patient often experiences the same feelings of fullness and satiety as would be experienced with an unrestricted stomach.

U.S. Pat. No. 5,771,903 issued to Jakobsson involves a method of gastric bypass surgery where the lower part of the esophagus is dissected and a band is applied around the lower part of the esophagus and an upper part of the stomach to form a small gastric pouch which upon filling with minimal food gives the patient a feeling of fullness or satiety. The band is inflatable and serves as a type of restrictor valve to regulate the amount of food passing from the banded upper gastric pouch to the unrestricted lower stomach. The band can be selectively inflated or deflated, depending upon the amount of food that is desired to be passed from the upper to lower stomach.

U.S. Pat. No. 6,572,627 issued to Gabbay discloses a system to inhibit the expansion of the stomach. The system involves placing a band about midway along the patient's stomach to create a restricted, smaller stomach. The system also employs a section of webbing that is placed around the upper half of the now restricted stomach. The webbing helps limit the expansion of the upper stomach.

Other inflatable band devices include the Lap Band™ System from Inamed Health of Santa Barbara, Calif.; the Heliogast™ gastric band from Helioscopie of Vienne Cedex, France; the Midband™ from Medical Innovation Development of Villeurbanne, France; and the Swedish Adjustable Gastric Band (SAGB) from Ethicon Endo-Surgery of the United States. These devices are placed around the stomach at its top or midpoint to create a smaller stomach.

The Proring® and Siliband® are gastric bands, both from Innovative Obesity Care of Saint Etienne, France, which require that the top of the stomach and esophagus first be stapled to form a small stomach pouch. The Proring® and Siliband® are then placed at the bottom of the pouch to form a restrictor valve for regulating the passage of food materials into the lower stomach. The Proring® has a closeable latch with a male-female engagement which is locked by the placement of a suture. The Siliband is closed and attached with sutures.

The prior art gastric band devices and their associated medical procedures have a success rate of about 65%, with many patients experiencing weight gain again after 5 years. Also, the following complications can result from existing devices and procedures.

First, the adjustable band devices can have a cross sectional contact width as large as 1" which has been found to cause the leakage of pouch contents into the peritoneal cavity, should these devices erode into the gastric pouch. The body is unable to form scar tissue around, and seal off, such a wide band device. This erosion problem is serious in that some deaths have occurred, and in lesser cases, these prior art bands have had to be removed, or else additional surgeries were necessary to repair leakage problems.

Second, the adjustable band devices have a tendency to accidentally enlarge, thereby letting more food through the restricted area than desired, and causing weight gain to return.

Therefore, a need exists for a gastric bypass band which does not promote leakage of pouch contents into the peritoneal cavity and which further does not accidentally enlarge, thereby allowing weight gain to return.

The foregoing reflects the state of the art of which the inventor is aware, and is tendered with a view toward discharging the inventor's acknowledged duty of candor, which may be pertinent to the patentability of the present invention. It is respectfully stipulated, however, that the foregoing discussion does not teach or render obvious, singly or when considered in combination, the inventor's claimed invention.

SUMMARY OF THE INVENTION

The invention is a method for performing gastric bypass surgery and an inventive gastric bypass band used along with the method.

The method of surgery involves separating the esophagus and a portion of the proximal stomach from the top of the remaining major portion of the stomach. The separated portion is used to form a small gastric pouch that can hold between 20-30 cc (about ⅛ cup) of food material. The inventive gastric bypass band is then placed in the mid-portion of the pouch to create a valve-like opening which will cause solid foods to stay in the gastric pouch for awhile, to give the sensation of a "full stomach." The band also prevents stomal dilation, that is the stoma, or opening between the pouch and small intestine (described further below) is prevented from dilating.

Still in reference to the inventive method, the small intestine is bisected to create a top section and a bottom section. Preferably, the top section includes the duodenum which retains all of its capability to receive liver bile, enzymes, and pancreatic secretions. The bottom section is connected to the bottom of the gastric pouch so that any food materials that pass by the gastric band restriction will empty directly into the small intestine for further digestion. The top section is then connected to the bottom section of the intestine which allows liver bile and pancreatic secretions from the top section to come into contact with the partially digested food materials that have been traveling from the gastric pouch down to the bottom section. Liver bile begins fat digestion for the first time and as a result, fats are only partially absorbed, contributing to greater weight loss.

The majority portion of the stomach comprising the remaining stomach and duodenum is completely separated from the manufactured digestive tract consisting of the gastric pouch and bottom section of the small intestine. The majority portion is sewed against the inner body cavity wall of the patient, and a radiopaque marker band is placed between the majority portion and the body cavity wall. A gastrostomy tube is placed through the marker band for immediate post operative care and the radiopaque marker band functions as a marker to locate this stomach site if it becomes necessary to place a gastrostomy tube for decompression or to feed the patient normally through the stomach or else to allow the surgery to be reversed and the stomach reconnected at a later date. The inventive gastric bypass band is also radiopaque.

The gastric band device which also comprises the invention is comprised of an expansion-resistant section that is attached to a latching mechanism. Preferably, the latching mechanism is of a one-way, male-female design, which comes together from opposite ends of the expansion-resistant section. When the latch is engaged, the band device assumes a radial shape which encircles the gastric pouch at a location selected by the surgeon. The radial shape and small width of the band helps prevent the device from becoming ingrown into the gastric pouch and/or causing tissue necrosis. The radial shape is best achieved if the opposite components of the latch are curved to aid in forming the radial shape upon joining the ends of the latch together.

It has been found that over time, using experimental fore runners of the inventive device and method, when employed together, resulted in patients maintaining their weight loss in 90% of the cases that are followed beyond 5 years post-surgery. This, compared with a success rate of only 65% of weight loss beyond 5 years post-surgery for the prior art gastric bypass surgery methods and banding devices, illustrates a large advantage of the inventive device and method.

As such, the following objects and advantages are sought to be achieved by the inventive gastric bypass band device and medical method:

An object of the invention is to provide a gastric bypass surgical method which bypasses the majority of the stomach and duodenum, thereby resulting in less post-surgery expansion of the gastric pouch.

Another object of the invention is to provide a gastric bypass band device which is available in multiple sizings to be able to meet any surgical situation.

Still another object of the invention is to provide a medical method and associated gastric band device which results in maintaining a 90% weight loss, beyond 5 years post-surgery, in morbidly obese patients.

Another object of the invention is to provide a device that can be easily placed and removed less invasively, laparoscopically, thereby reducing surgical recovery time to around three weeks.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings which are for illustrative purposes only:

FIG. 3 is an elevated perspective view of the inventive gastric bypass band shown in its engaged state.

FIG. 4 is a cross sectional view through the expansion resistant section of the inventive gastric bypass band.

FIG. 5A is a closeup elevated perspective view of the female portion of the latch.

FIG. 5B is a closeup elevated perspective view of the male portion of the latch.

FIG. 5C is a closeup elevated perspective view of the male portion of the latch fully engaged within the female portion.

FIG. 6 is a side view of the gastric bypass band device shown in an engaged position, illustrating the radial shape of the device.

FIG. 7A is a side view of a protective cover for engaging with the female portion of the gastric bypass band device.

FIG. 7B is a front elevated perspective view of the cover.

FIG. 8 is an elevated perspective view of the radiopaque marker band of the present invention.

DETAILED DESCRIPTION OF THE PREFERRED EMBODIMENTS

Figure 1:
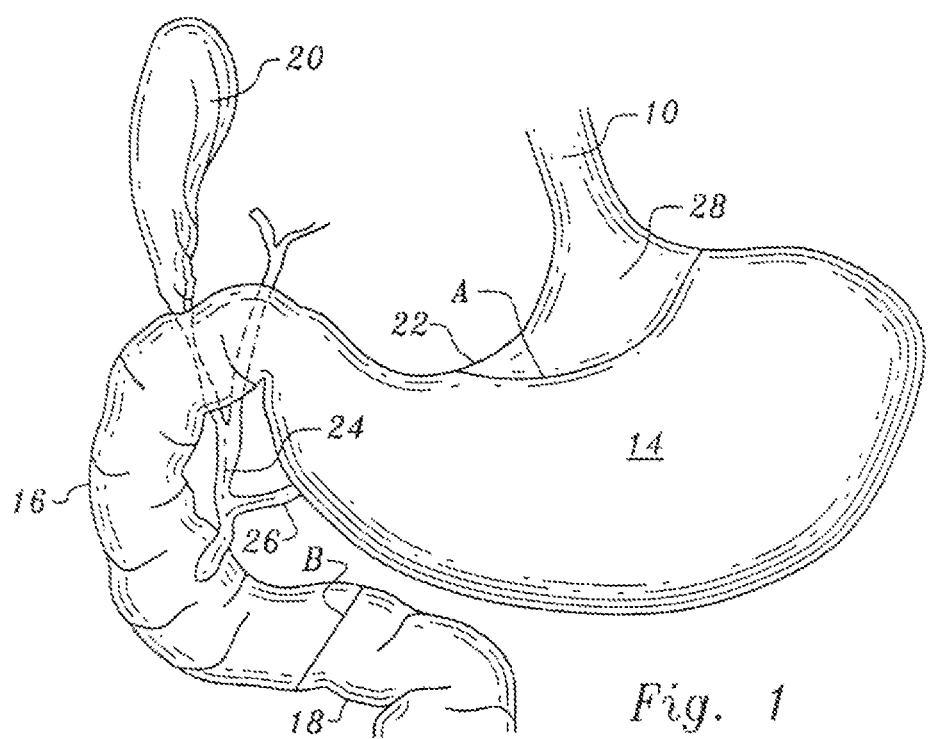
FIG. 1 is a frontal view of a human esophagus, stomach and partial small intestine to illustrate the body locations near the esophagus and small intestine where the inventive medical procedure is performed.
Figure 2:
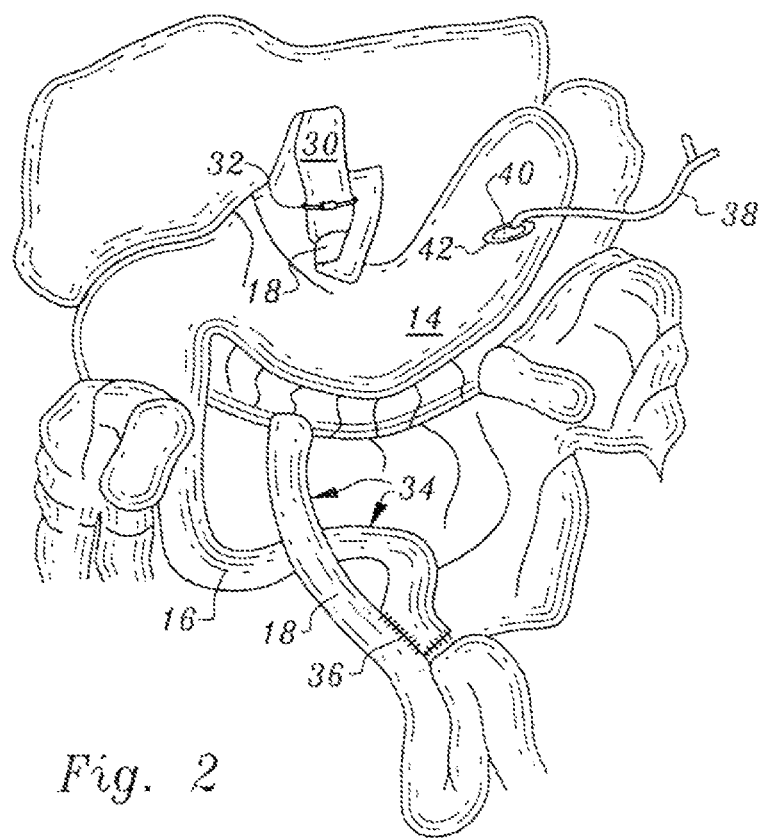
FIG. 2 is a frontal view of a human body cavity showing the esophagus connected to the lower portion of the small intestine and the upper portion of the small intestine, containing the duodenum, being connected to the lower portion of the small intestine.

Referring to FIGS. 1 and 2, the preferred embodiment of the inventive medical method can be shown. The medical method is performed laparoscopically in 90% of the cases. In FIG. 1, the organs of the esophagus 10, stomach 14, duodenum 16, small intestine 18 and gall bladder 20 are shown. The focus of the medical method is upon the modifications made to the esophagus 10, stomach 14 and small intestine 18. As first shown in FIG. 1, a gastric pouch is manufactured by preferably separating the esophagus 10 and part of the lesser curvature 22 of the stomach from the remainder of the stomach 14 at point A. The small intestine 18 is bisected at point B. The location of point B is preferred because it results in the duodenum 16 being completely bypassed along with the stomach 14. Bypassing the duodenum results in selective fat malabsorption which results in more weight loss than in prior art gastric bypass methods. The duodenum remains fully functional and continues to receive liver bile from the hepatic ducts 24 and enzymes from the pancreatic duct 26.

Referring now to FIG. 2, the formation of the gastric pouch and the re-connection of the small intestine can be described. The proximal stomach is bisected on the lesser curvature 22 just below the esophagus 10, leaving a small stomach segment 28 that is connected to the proximal jejunum 18, this esophogeal and small stomach segment is what will eventually form the gastric pouch 30 having a size of between 20-30 cc. The bottom section of the small intestine (proximal jejunum) 18 below the duodenum 16 is connected to the small stomach segment 28 through a hand sewn closure to form an anastomosis (not shown) that is 1.5 to 2 cm wide. The anastomosis is impervious to air and water and allows direct entry of the contents of the gastric pouch 30 into the small intestine 18, which causes the release of satiety stimulating chemicals known as enterokinins. This release of enterokinins is even induced by the obese individual's salivary secretions that go from the gastric pouch 30 to the small intestine 18. This feeling of satiety, or "fullness" results in anorexia and enhances initial weight loss as well as the maintenance of weight loss over time.

Above the anastomosis and above the bottom of the pouch 30, about 2 cm, is placed the inventive gastric bypass band device 32. The gastric band device acts as a restrictor valve which controls the emptying of partially digested food materials from the gastric pouch 30. The gastric band 32 is preferably placed at the distal portion of the gastric pouch 30. When the inventive gastric band is in place, the portion of the pouch above the gastric band is 15 to 20 cc in capacity and the portion of the pouch below the band is about 8 to 10 cc in capacity. This compared to the normal 2000-3000 cc capacity of the stomach illustrates the restriction in food intake provided by the gastric pouch. Once the gastric pouch is full of food materials, a feeling of satiation is experienced, resulting in anorexia. The gastric band device 32 preferably ranges in size between 5.5-7.0 cm in inner circumference. In addition to its function as a restrictor valve, the gastric band 32 prevents stomach dilation, meaning that the restricted opening provided by the band never expands in size due to the expansion-resistant construction of the device. Moreover, the pouch 30 is more resistant to expansion than the stomach. The relative size of the pouch ensures that excessive expansion does not occur. Patients that have been X-rayed five years post-surgery show that the pouch has not expanded by much. Moreover, the small size of the pouch insures that if a patient over-eats, the food will back up into the esophagus, thereby causing the patient to regurgitate the food. This factor operates as a self-regulating feature, and for this reason, patients are counseled to keep their food intake to a minimum.

The duodenum 16 is re-joined to the small intestine 18 to form a Y-limb 34, with one deviation of the limb going upward to the duodenum and the other deviation proceeding upward to the gastric pouch 30. The intestine-intestine connection 36 forms an anastomosis (not shown) of approximately 2 cm, that is wide enough to allow food to pass through easily. At the point of anastomosis, pancreatic juices and liver bile from the duodenum can now come into contact with the partially digested food that travels down the second section of the intestine from the pouch. Liver bile begins fat digestion for the first time, and as a result, fats are only partially absorbed, thereby helping contribute to weight loss. Sugars are absorbed, but discouraged as part of the patient's diet, because with the stomach disconnected, they go directly into the intestines, causing some patients to have "Dumping Syndrome." This is a very uncomfortable feeling of cramps, flushing, fast beating heart, weakness and sometimes watery stools.

The stomach 14, although disconnected, remains fully functional, and if necessary can be reactivated by reversing the surgery and re-connecting the stomach segment 28 and small intestine 18 to their prior, natural, state. The stomach 14 can also be reactivated by placing a temporary gastrostomy tube 38, as shown, through which food can be routed, should this be necessary. To facilitate the reactivation of the stomach 14, the stomach opening 40 can be marked with a radiopaque marker band 42 or disk, that is sutured to the abdominal wall, thereby making it clearly visible to allow the surgeon to find the stomach entry site 40 on an X-ray, to allow easy reactivation.

The inventive gastric bypass band device 32 that was introduced previously, as being crucial to the successful result of the inventive surgical method, will now be described in terms of its preferred embodiment. Referring to FIG. 3, the gastric bypass band 32 is comprised of an expansion-resistant section 44 mated to a latch 46, which locks upon full engagement, thereby preventing the device 32 from opening up while positioned within the body. The latch 46 is of a one-way variety and can only be released through the application of a specialized surgical tool (not shown). The expansion-resistant section 44 prevents the device from expanding too far, thereby restricting the amount of food traveling from the gastric pouch 30 to the small intestine 18. It is important for the device to retain food within the pouch long enough for the patient to feel sated, thereby reducing hunger and preventing further eating. The expansion-resistant section 44 is preferably made from implant grade silicone rubber surrounding a monofilament core. The monofilament can be polypropylene suture material, which is resistant to expansion. The latch is preferably made from surgical-grade plastics such as polypropylene or acetal, which gives both strength and lubricity to the latch.

FIG. 4 shows a transverse cross section of the expansion-resistant section 44 which illustrates the monofilament core 48 surrounded by silicone material 50. Alternatively, the silicone material can be a silicone tube having a monofilament core therein. The expansion-resistant section 44 preferably has a flat-faced inner side 52 as shown. This flat face 52 continues longitudinally along the length of the expansion-resistant section 44. The flat face 52 forms a flat-sided inner circumference when the latch of the device is engaged, as shown in FIG. 3. It has been found that the flat face prevents the expansion-resistant section from migrating into the patient's tissue and prevents tissue erosion. Also crucial with regard to preventing leakage caused by the device eroding into the internal lumen of the gastric pouch is that the cross-sectional diameter of the expansion-resistant section 44 is kept to 0.125", or less. If erosion occurs, it has been found that if the cross section is kept to these approximate dimensions the pouch tissue will form a scar around the band device 32, and in essence seal off the device, thereby preventing any leakage.

Erosion is caused by tissue necrosis, where tissue dies when the supply of blood to the area is cut off. Prior art larger, thicker, band devices, have been known to necrose when the food pouch begins to sag, making a deep sack out of which food has difficulty being passed. This food begins to decay in the pouch, which can lead to necrotic complications. The larger, thicker, prior art devices penetrate the necrosed area in time, creating a break in the gastric pouch, which can lead to leakage of the pouch contents into the interior of the body cavity. In the worst cases this can lead to death; in the minor cases, additional surgery is necessary to repair the breached pouch. Contrastingly, fewer pouch breaches are experienced with the present invention than with the prior art devices.

Referring now to FIGS. 5A, 5B and 5C the latch 46 can be examined. The latch is preferably a one-way latch employing a one-way male-female engagement. The opposite ends 54, 56 of the expansion-resistant section 44 are each mated to one-half of the male-female latch as shown in FIG. 3 and a preferred method of mating is further described below.

As shown in FIG. 5A, the female portion 58 of the latch 46 is illustrated in detail. The female portion has an exterior body 60 and an interior lumen 62 for receiving the male portion 64 of the latch. The lumen 62 is sized to compress the lateral prongs 66 of the male portion 64. Under surgical conditions, engagement of the male and female portions is performed with a forceps, laparoscopically. The preferred interior lumen 62 dimensions are approximately height=0.082"× width=0.190×length=0.300". A pair of openings 68 are placed in each side 70 of the female portion 58 to allow for the expansion of the lateral catches 72 of the male portion 64. The lateral catches 72 engage fully and laterally within the side openings 68, in a one-way fashion. Side openings 68 have top, bottom, rear and front walls, which engage catches 72. The engagement is such that the latch can be released only after applying a special surgical tool (not shown) to disengage the latch 46, by placing inward force upon catches 72 through side openings 68. The lumen 62 opens outward and the face 74 of the opening of the lumen is inwardly beveled so as to receive the outward bevels 76 of the male portion 64. The corner facings 78 of the female portion 58 are rounded so as to present a non-irritating surface to the patient.

Still referring to FIG. 5A, the body 60 of the female portion 58 is longitudinally curved 80. The curvature of the female portion 58 mates with the longitudinally curved male portion 64 to form the device 32 into a radial shape as shown in FIG. 6. This radial shape is crucial for preventing the device from becoming ingrown within a patient's tissue, as this shape applies equal pressure to the enclosed tissue at every point along the inside circumference of the device 32. Shapes that are non-circular (e.g. oblong shapes) tend to apply unequal pressure along their inside circumference, thereby resulting in a cutoff of blood supply, necrosis, and eventual tissue erosion and leakage as discussed previously. For each graduation in inner circumference of the inventive device 32, a corresponding radius of curvature applies which contributes to the forming of the proper radial shape in each case. The radii of curvature in inches is listed after each graduation in inner circumference (centimeters) as follows: 5.5 cm=5.5 cm=0.398"; 6.0 cm=0.422"; 6.5 cm=0.460" and 7.0 cm=0.492". Also, for the same graduations, the following diameters apply: 5.5 cm=1.75 cm dia; 6.0 cm=1.91 cm dia; 6.5 cm=2.07 cm dia; 7.0 cm=2.23 cm dia. The inner circumference that is used is open to the discretion of the surgeon, but generally, men require 6.5 and 7.0 cm sizes while women require 5.5 and 6.0 cm devices.

Referring now to FIG. 5B, the male portion of the latch is shown as comprising a pair of lateral prongs 66, the prongs being longitudinally curved to mate efficiently within the lumen 62 of the female portion 58. Preferably, prongs 66 are approximately 0.076" thick, by 0.040" wide. The prongs terminate at their front with lateral catches 72 which are molded integrally with the prongs 66. Lateral catches 72 are angled longitudinally along their side face 84, the angled attitude allowing easy entry of the prongs 66 into the lumen 62 of the female portion 58, which is an important feature under surgical conditions. Side faces 84 having steeper angles give a mechanical advantage when locking. The preferred angle of side faces is 36 degrees or less. The catches 72 further comprise lateral catch faces 86, which engage the front walls of the side openings 68 of the female portion 58. When the catches 72 of prongs engage, it is preferred that they remain engaged under a pulling stress of at least 5 pounds of force. The prongs 66 are separated by inner space 88, which allows the prongs to travel inward and outward. The prongs 66 terminate rearwardly at prong body 90, which provides a base of structural integrity from which prongs can confidently travel inward and outward as they engage the interior walls of lumen. Prong body 90 migrates further rearward to become outwardly beveled face 76 which mates with inwardly beveled face 74 of the female portion 58. The beveled face 76 migrates further rearward to become hilt 92. Hilt 92 is where the front opening of the female portion 58 fully engages against. This engagement is shown in FIG. 5C which illustrates lateral catches 72 seated in the side openings 68 of female portion 58, the hilt being 92 engaged with the front opening of female portion. The circumference of the body 60 of female portion 58 and the circumference of the hilt 92 of the male portion 64 are preferably identical so as to provide a fairly uninterrupted surface traveling from one to the other.

Also shown in FIGS. 5A and 5B are anchor arms 94, which are used to attach the male and female portions of latch to the expansion-resistant section 44. Anchor arms 94 retain the curved theme of the male and female portions, 58, 64 of the latch 46. Anchor arms 94 are molded integrally with their corresponding latch portion and curve rearwardly so as to retain the radii of curvature of the inventive device noted previously. The expansion-resistant section which is comprised of surgical grade silicone and monofilament is attached to the anchor arms as follows. Referring again to FIG. 5B, the front opening 96 of lumen 98 is shown, and its rearward path of travel through anchor arm is shown in phantom. A similar arrangement exists for female portion. Monofilament 48 enters the rear of anchor arm and is fed through lumen until it protrudes through the front opening of lumen. The monofilament 48 is then tied off in a manner so as to anchor it in place along with the silicone material as seen in phantom, in FIG. 3.

As FIGS. 7A-7B show, the body 60 of female portion 58 may also be fitted with a disposable cover 100 so as to reduce its potential to snag upon tissue as it is being fed through and positioned around the gastric pouch 30 during laparoscopic surgery. As the device is fed through the tissue and around the new pouch, it is led by the female portion 58. Cover 100 provides a streamlined shape which can be grasped by a forceps and easily led through the tissue. FIG. 7A is a side view showing the female end 58 positioned in the cover 100, with the remainder of the device trailing out the back end 102 of cover 100. Back end 102 of cover includes a lumen (see FIG. 7B) 104 for receiving female end 58, the lumen being sized to snugly grasp female end without coming loose during surgical placement. The sides of lumen are preferably ringed with small ridges 106 to reduce the frictional engagement between female portion 58 and the cover 100 to a level that allows easy removal of the cover once the device is in place. As seen in FIG. 7B, cover 100 further comprises a blunt front end 108 which extends into an elongate portion 110. The blunt front end 108 facilitates easy movement through tissue. The elongate portion 110 is for grasping by the surgeon's forceps to allow the cover to be threaded through tissue. Past the elongate portion 110, the cover 100 has a gently tapered region 112, which, again contributes to easy movement through tissue. At its widest point, the cover is about 0.250 to allow easy movement through a trocar during laparoscopic surgery. The cover is preferably made from a radiopaque material for easy sighting on an X-ray. The cover is removed and discarded once the device has been positioned around the gastric pouch.

Referring now to FIG. 8, the radiopaque marker band 42 previously shown in FIG. 2 can be more precisely described. The band's inside diameter is approximately 0.8" and the outside diameter is approximately 1" with a thickness of approximately 0.06". The band is preferably flat along its major surfaces 114, 116. The marker band 42 can be made from polyester mesh that is coated with surgical grade silicone. Also, it is envisioned by the inventor that the inventive device 32 can be combined with the radiopaque marker band 42 shown in FIG. 8, as well as with the disposable cover 100 to form a surgical kit. This kit can then be installed surgically using the method previously described.

Finally, although the description above contains many specificities, these should not be construed as limiting the scope of the invention but as merely providing illustrations of some of the presently preferred embodiments of this invention. Other modifications by those skilled in this art are possible and are included within the scope of the appended claims.

The invention claimed is:

1. A surgical band device that is laparoscopically implantable within a patient's body, comprising:
 a flexible expansion-resistant section having first and second ends, the expansion-resistant section having a flat face extending along its length between the first and second ends, the expansion-resistant section being of uniform-cross section between the first and second ends; and
 a lockable latch having first and second latch parts coupled to the first and second ends of the expansion-resistant section;
 wherein the first and second latch parts have a fixed longitudinal curvature when the first and second latch parts are unlocked; and wherein the expansion-resistant section having a longitudinally extending configuration along its length when the first and second latch parts are unlocked and the surgical band device is fed laparoscopically through tissue within the patient's body and a radial shape configuration along its length when the first and second latch parts are locked and the surgical band device is positioned around tissue within the patient's body;
 wherein the first latch part of the lockable latch including an exterior body having an interior lumen, said exterior body having side through-openings communicating with said lumen, said lumen including a front opening, wherein said front opening is lined with an inwardly-beveled face;
 wherein the first and second latch parts of said lockable latch are engaged by a male-female type engagement;
 wherein the second latch part of the lockable latch including two lateral prongs extending from a prong body, said prong body having an outwardly-beveled face, said lateral prongs extending forward of said prong body and ending in two corresponding lateral catches, said lateral catches including angled side faces for engaging with said lumen of said first latch part, said lateral catches further engaging in a lockable one-way engagement with said side openings of said first latch part when said first and second latch parts are fully engaged and wherein upon full engagement, said outwardly-beveled face of said second latch part mates with said inwardly beveled face of said first latch part.

2. The band device as recited in claim 1, wherein the expansion-resistant section comprises a length of silicone having a monofilament core.

3. The band device as recited in claim 2, wherein the monofilament core is a polypropylene suture.

4. The band device as recited in claim 3, wherein the device is radiopaque.

5. The band device as recited in claim 1, wherein the latch locks in a one-way engagement.

6. A surgical kit, comprising:
 a gastric bypass band device that is laparoscopically implantable within a patient's body, comprising:
 a flexible expansion-resistant section having first and second ends, the expansion-resistant section having a flat face extending along its length between the first and second ends, the expansion-resistant section being of uniform-cross section between the first and second ends; and
 a lockable latch having first and second latch parts coupled to the first and second ends of the expansion-resistant section; wherein the first and second latch parts have a fixed longitudinal curvature when the first and second latch parts are unlocked; and wherein the expansion-resistant section having a longitudinally extending configuration along its length when the first and second latch parts are unlocked and the surgical band device is fed laparoscopically through tissue within the patient's body and a radial shape configuration along its length when the first and second latch parts are locked and the surgical band device is positioned around tissue within the patient's body;
 a radiopaque marker band; and
 a disposable positioner cover fitted over the second latch part and having a blunt forward profile for guiding the gastric band device into position about tissue in a patient's body.

7. The surgical kit as recited in claim 6, wherein the band device, and the disposable cover are radiopaque.

8. The surgical kit as recited in claim 6, wherein the positioner cover further comprises a lumen for receiving the second latch part, the lumen of the positioner cover being lined with longitudinal ridges.

9. The cover as recited in claim 8, wherein the lumen forms a rear opening in the positioner cover, the lumen portion extending forward and mating with an elongate portion of the positioner cover, the elongate portion terminating in a blunt forward end.

* * * * *